US005552537A

United States Patent [19]
Saxon et al.

[11] Patent Number: 5,552,537
[45] Date of Patent: Sep. 3, 1996

[54] IGE ISOFORMS AND METHODS OF USE

[75] Inventors: Andrew Saxon, Santa Monica; Ke Zhang, Los Angeles, both of Calif.; Edward E. Max, Bethesda, Md.

[73] Assignee: The Regents of the University of California, Oakland, Calif.

[21] Appl. No.: 37,579

[22] Filed: Mar. 24, 1993

[51] Int. Cl.$^6$ .................. C07H 21/04; C07H 21/02; C12Q 1/68

[52] U.S. Cl. .............. 536/24.3; 536/22.1; 536/23.1; 536/24.31; 536/24.33; 435/6

[58] Field of Search ............... 536/22.1, 24.3, 536/24.31, 23.1, 24.33

[56] References Cited

FOREIGN PATENT DOCUMENTS

WO91/11456  8/1991  WIPO.

OTHER PUBLICATIONS

Hamilton and Adkinson (1992) "Measurement of total serum immunoglobulin E and allergen–specific immunoglobulin E antibody", pp. 689–701, In Rose, et al. (ed.s), *Manual of Clinical Laboratory Immunology*, Fourth Edition, American Society for Microbiology, Washington, D.C.

Hellman (1993) "Characterization of four novel ε chain mRNA and a comparative analysis of genes for immunoglobulin E in rodent and man", *Eur. J. Immunol.*, 23:159–167.

Nissim et al. (1993) "Fine specificity of the IgE interaction with the low and high affinity Fc Receptor", *J. Immunol.*, 150:1365–1374.

Peng et al. (1992) "A new isoform of human membrane–bound IgE", *J. Immunol.*, 148(1):129–136.

Robertson et al. (1990) "Human IgE–binding Protein: A soluble lectin exhibiting a highly conserved interspecies sequence and differential recognition of IgE glycoforms", *Biochemistry*, 29(35):8093:8100.

Sun et al. (1991) "Transfectomas expressing both secreted and membrane–bound forms of chimeric IgE with antiviral specificity", *J. Immunol.*, 146(1):199–205.

Zhang et al. (1992) "Two unusual forms of human immunoglobulin E encoded by alternative RNA splicing of ε heavy chain membran exons", *J. Exp. Med.*, 176:233–243.

Zhang et al, (Feb. 1992), "Alternative splicing of exons downstream of the human IgE constant region gene yields mRNAs encoding a membrane–bound form of IgE and a large secreted form", Fed. Am. Soc. Exp. Biol. 6(4):A1153.

Zhang et al, (Mar. 6, 1992), "Epsilon mRNAs encoding novel secreted and membrane IgE results from splicing variants in IgE producing human cells", J. Allergy Clin. (Mar. 6, 1992) Immunol. 89(1 part 2) 174.

Efremov et al, (Aug. 1993), "Molecular analysis of IgE H–chain transcripts expressed in vivo by peripheral blood lymphocytes from normal and atopic individuals", J. Immunol. 151:2195–2207.

(List continued on next page.)

Primary Examiner—W. Gary Jones
Assistant Examiner—Jeffrey Fredman
Attorney, Agent, or Firm—Bertram I. Rowland; Pamela J. Sherwood

[57] ABSTRACT

Methods and compositions are provided relating to novel IgE isoforms and their use in immune hypersensitivity diagnosis and treatment. The compositions include transcription and translation products of the immunoglobulin epsilon locus, specific probes for epsilon transcription products, and compounds which specifically bind epitopes of epsilon translation products. Novel products of the epsilon locus include the following transcription products and translation products thereof: CH4-M2", SEQ ID NO:02, residues 1-107 and, (SEQ. ID NO:06, CH4'-CH5-M1'-M2, (see SEQ ID NO:02, residues 1-72,SEQ ID NO:03 and SEQ ID NO:05) CH4'-CH5-M2'(SEQ ID NO:02, residues 1-72, SEQ ID NO:03 and SEQ ID NO:07 and CH4'-CH5-M2" (SEQ ID NO:02, residues 1-72, SEQ ID NO:03 and SEQ ID NO:06). Such epsilon products, specific probes and binding compounds find use in methods and kits for immune hypersensitivity diagnosis and treatment.

8 Claims, 6 Drawing Sheets

OTHER PUBLICATIONS

Seno et al, (1983), "Molecular cloning and nucleotide sequencing of human immunoglobulin e chain cDNA", Nucleic Acids Res. 11(3):719–726.

Peng et al, (1990), "Alternative mRNA splicing in the transmembrane segment of human e immunoglobulin", Fed. Am. Soc. Exp. Biol. 4(7):A1808.

Max et al, (1982), "Duplication and deletion in the human immunoglobulin e genes", Cell 29:691–699.

Flanagan et al, (1982), "The sequence of a human immunoglobulin epsilon heavy chain constant region gene and evidence for three non–allelic genes" EMBO J. 1(5):655–660.

Zhang et al, (1994), "Complex alternative RNA splicing of e–immunoglobulin transcripts produces mRNAs encoding four potential secreted protein isoforms", J. Biol. Chem. 269(1):456–462.

```
GCCGCGGTGCTGCCCCGGAAGTCTATGCGTTTGCGAATCAGCCGGGAGTGGCCGGGGAGCCCACCCTGCCTGATCCAGAACTTCATGCC
 ProArgAlaAlaProGluValTyrAlaPheAlaThrProGluTrpProGlySerArgAspLysProGlyThrLeuAlaCysLeuIleGlnAsnPheMetPro
TGAGGACATCTCGGTGCAGTGCTGCACAACGAGGTGCAGCTCCCGGACGCCCGGACCAAGACCAAGGGCTCCGGCTTCTTC
 GluAspIleSerValGlnTrpLeuHisAsnGluValGlnLeuProAspAlaArgHisSerThrThrGlnProArgLysThrLysGlySerGlyPhePhe
GTCTTCAGCCGCCTGGAGGTGACCAGGGCGAATGGGAGAAAAGATGAGTTCATCTGCCGTGCAGTCCATGAGGCAGTCCCCTCAGAGCCGTC
 ValPheSerArgLeuGluValThrArgAlaGluTrpAlaGluLysAspGluPheIleCysArgAlaValHisGluAlaAlaSerProSerGlnThrVal
AGGGAGGGTGTCTGTAAATCCCGGTAAAATGACGTACTCCTGCCTCCCCCAGGCTCCATCCAGTGTGAGTGGGAGGACTGGCCAGACCTT
 GlnArgGlyValCysValAsnProGlyLys***          GlySerIleGlnLeuCysSerGlyGlyGluAspTrpProAspLeu
CTGTCCACTGTTGCAATGACCCCAGGAAGCTACCCCCAATAAACTGTGCCTGCTCAGAGCCCCAGTACACCCATTCTTGGGAGCGGGGCAGGGGCTGTGGG
 LeuSerThrValAlaMetThrProGlySerTyrProGln***
```

```
         10        20        30        40        50        60        70        80        90       100
         |         |         |         |         |         |         |         |         |         |
CATGGTGGGCACCCACCTCCAGGGGCCCAGGGCCAGGGGCAGGGGTTGGGCAGAGACCAGAGAGCCCCTGACCCACCGCCCTCCCCTCAGGTGCAGCGGTTC     M2
                                                                                       ValGlnArgPhe      M2'
                                                                                          6   GlyAlaAlaVal
        110       120       130       140       150       160       170       180       190       200
         |         |         |         |         |         |         |         |         |         |
LeuSerAlaThrArgGlnGlyArgProGlnThrSerLeuAspTyrThrAsnValLeuGlnProHisAla***                                 M2
CTCTCAGCCACGCGGGCAGGGGAGGCCCAGGCCCAGAGCCCCTGACCTACACCAACGTCCTCCAGCCCCACGTCCTAGGCCCGGGCCACTCACGCTCCACCAGGC
ProLeuSerHisAlaAlaAlaGlyGluAlaGlyProProArgLeuHisGlnArgProProAlaProArgLeuGlyArgProLeuThrLeuHisGlnAla     M2'
        210       220       230       240       250       260       270       280       290       300
         |         |         |         |         |         |         |         |         |         |
CCAGCTTTTCTCTGCCCTGAGCCTGAACCTGAGCCTCCCTCGGGCTGCCCTGCACCCTGGGTGGGAAAAGGGAAGCAGAAGACAAGAAAAAGGGGCACAAGGTCACTAC
GlnLeuPheLeuCysGlnLeuSerLeuProArgLeuProCysProArgAlaAlaLeuHisProGlyTrpGlyLysGlySerArgGlnGluLysGlyAlaGlnGlyHisTyr
        310       320       330       340       350       360       370       380       390       400
         |         |         |         |         |         |         |         |         |         |
TGTGGGCTGATGGCCAGTGAACCTGAGCCCGGAGGGCAGGGCCGGCTCAGCCAAGGTTACAGGCGCCGAGAGAACCACCAGTGCCAGGCCCCACCCGAAAAC
CysGlyLeuMetAlaSerGluProGluProGlyGlyGlnGlyArgLeuSerGlnGlyLeuGlnLeuGlnAlaArgGluAsnHisGlnCysGlnAlaProThrArgLys
        410       420       430       440       450       460       470       480       490       500
         |         |         |         |         |         |         |         |         |         |
       GluSerSerArgGlyGlyCys***                                                                         M2
CGTGTCTGTCCCTTCAACAGAGTCATGAGCGAGGGGTGGCTGCTGTAGCCTGGTTCTGAGCTCATCCCAGGCCGTTCTGAGGTCTCCGGGTCACTCCATTCTGACT
ProCysLeuSerLeuGlnGlnSerHisGluSerArgSerGluLeuIleProGlyProTrpValSerGlyLeuProPhe***                        M2'
                                                                                 7
        510       520       530       540       550       560       570       580       590       600
         |         |         |         |         |         |         |         |         |         |
CGGGGACCAGCCCCGGGCACCCGCCCCCCAGCCCCAACACCCAGCCTGAGTCTGCGTCCAGGGCACAGCTGAGTCTGCGTCCAGCCCAACACCCAGGGCCTCACTCCCCAGCCT
        610       620       630       640       650       660       670       680       690       700
         |         |         |         |         |         |         |         |         |         |
GTACAATCACCACCAAAAGCCAAGGAGGGGCCCGGCACCCGGGCACCCGGGGCACCCGTCCCCAAGCCTGCATCCCCGTCCCCCAAGCCCCAGAGCTTCTTCCTTCACCCACCCCTCCTGCCACCC
CGGTCTGACCCTTCTAGCCCTGAGATCCAAGTGCCTGCATCCCCGTCCCCAAGCCCCAGACCTTCTTTCCCTTCACCCCTCCTGCCACCC
                                                 8
```

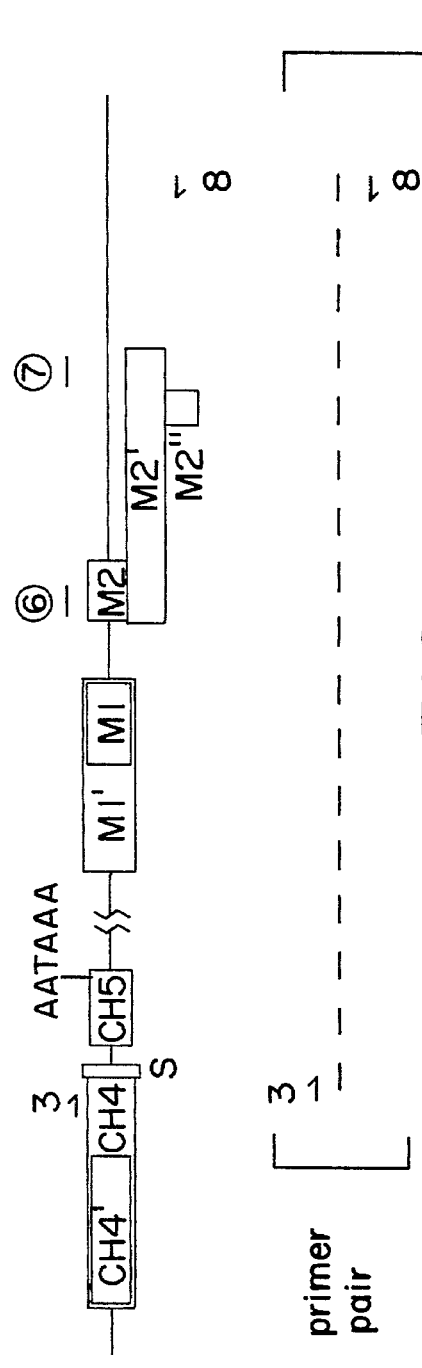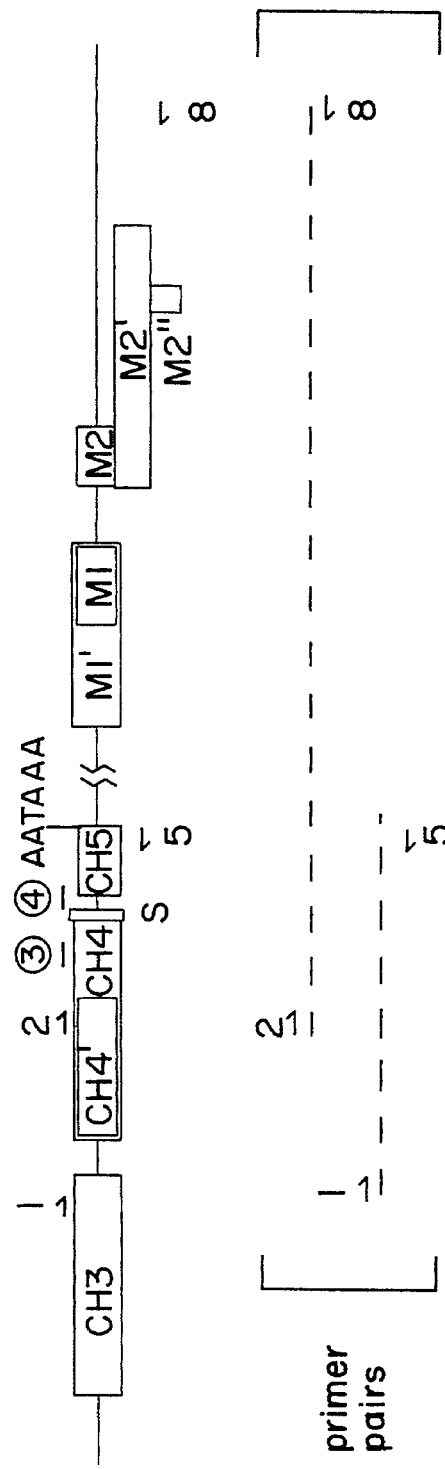

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 500 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 3..329

( i x ) FEATURE:
        ( A ) NAME/KEY: CDS
        ( B ) LOCATION: 359..439

( x i ) SEQUENCE DESCRIPTION: SEQ ID NO:1:

```
GC  CCG  CGT  GCT  GCC  CCG  GAA  GTC  TAT  GCG  TTT  GCG  ACG  CCG  GAG  TGG         47
    Pro  Arg  Ala  Ala  Pro  Glu  Val  Tyr  Ala  Phe  Ala  Thr  Pro  Glu  Trp
     1              5                        10                       15

CCG  GGG  AGC  CGG  GAC  AAG  CGC  ACC  CTC  GCC  TGC  CTG  ATC  CAG  AAC  TTC         95
Pro  Gly  Ser  Arg  Asp  Lys  Arg  Thr  Leu  Ala  Cys  Leu  Ile  Gln  Asn  Phe
               20                       25                       30

ATG  CCT  GAG  GAC  ATC  TCG  GTG  CAG  TGG  CTG  CAC  AAC  GAG  GTG  CAG  CTC        143
Met  Pro  Glu  Asp  Ile  Ser  Val  Gln  Trp  Leu  His  Asn  Glu  Val  Gln  Leu
               35                       40                       45

CCG  GAC  GCC  CGG  CAC  AGC  ACG  ACG  CAG  CCC  CGC  AAG  ACC  AAG  GGC  TCC        191
Pro  Asp  Ala  Arg  His  Ser  Thr  Thr  Gln  Pro  Arg  Lys  Thr  Lys  Gly  Ser
               50                       55                       60

GGC  TTC  TTC  GTC  TTC  AGC  CGC  CTG  GAG  GTG  ACC  AGG  GCC  GAA  TGG  GAG        239
Gly  Phe  Phe  Val  Phe  Ser  Arg  Leu  Glu  Val  Thr  Arg  Ala  Glu  Trp  Glu
      65                       70                       75

CAG  AAA  GAT  GAG  TTC  ATC  TGC  CGT  GCA  GTC  CAT  GAG  GCA  GCG  AGC  CCC        287
Gln  Lys  Asp  Glu  Phe  Ile  Cys  Arg  Ala  Val  His  Glu  Ala  Ala  Ser  Pro
 80                       85                       90                       95

TCA  CAG  ACC  GTC  CAG  CGA  GCG  GTG  TCT  GTA  AAT  CCC  GGT  AAA                   329
Ser  Gln  Thr  Val  Gln  Arg  Ala  Val  Ser  Val  Asn  Pro  Gly  Lys
                    100                      105

TGACGTACTC  CTGCCTCCCT  CCCTCCCAG   GGC  TCC  ATC  CAG  CTG  TGC  AGT  GGG             382
                                   Gly  Ser  Ile  Gln  Leu  Cys  Ser  Gly
                                     1                    5

GAG  GAC  TGG  CCA  GAC  CTT  CTG  TCC  ACT  GTT  GCA  ATG  ACC  CCA  GGA  AGC        430
Glu  Asp  Trp  Pro  Asp  Leu  Leu  Ser  Thr  Val  Ala  Met  Thr  Pro  Gly  Ser
      10                       15                       20

TAC  CCC  CAA   TAAACTGTGC  CTGCTCAGAG  CCCCAGGTAC  ACCCATTCTT                         479
Tyr  Pro  Gln
 25

GGGAGCGGGC  AGGGCTGTGG  G                                                              500
```

( 2 ) INFORMATION FOR SEQ ID NO:2:

( i ) SEQUENCE CHARACTERISTICS:
        ( A ) LENGTH: 109 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Pro Arg Ala Ala Pro Glu Val Tyr Ala Phe Ala Thr Pro Glu Trp Pro
 1               5                  10                  15

Gly Ser Arg Asp Lys Arg Thr Leu Ala Cys Leu Ile Gln Asn Phe Met
            20                  25                  30

Pro Glu Asp Ile Ser Val Gln Trp Leu His Asn Glu Val Gln Leu Pro
            35                  40                  45

Asp Ala Arg His Ser Thr Thr Gln Pro Arg Lys Thr Lys Gly Ser Gly
        50                  55                  60

Phe Phe Val Phe Ser Arg Leu Glu Val Thr Arg Ala Glu Trp Glu Gln
 65                  70                  75                  80

Lys Asp Glu Phe Ile Cys Arg Ala Val His Glu Ala Ala Ser Pro Ser
                85                  90                  95

Gln Thr Val Gln Arg Ala Val Ser Val Asn Pro Gly Lys
                100                 105
```

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Gly Ser Ile Gln Leu Cys Ser Gly Glu Asp Trp Pro Asp Leu Leu Ser
 1               5                  10                  15

Thr Val Ala Met Thr Pro Gly Ser Tyr Pro Gln
            20                  25
```

( 2 ) INFORMATION FOR SEQ ID NO:4:

( i ) SEQUENCE CHARACTERISTICS:
        ( A ) LENGTH: 700 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 89..172

( i x ) FEATURE:
        ( A ) NAME/KEY: CDS
        ( B ) LOCATION: 420..446

( x i ) SEQUENCE DESCRIPTION: SEQ ID NO:4:

```
CATGGTGGGC ACCCACCTCC AGGGGCCCAG CCAGGGCAGG GGGTTGGGCA GAGCCAGCAG      60

AGCGCCCTGA CCCACGCCCT CCCCTCAG GTG CAG CGG TTC CTC TCA GCC ACG        112
                                Val Gln Arg Phe Leu Ser Ala Thr
                                 1               5

CGG CAG GGG AGG CCC CAG ACC TCC CTC GAC TAC ACC AAC GTC CTC CAG       160
Arg Gln Gly Arg Pro Gln Thr Ser Leu Asp Tyr Thr Asn Val Leu Gln
        10                  15                  20

CCC CAC GCC TAGGCCGCGG GCCACTCACG CTCCACCAGG CCCAGCTTTT               209
Pro His Ala
 25

TCTCTGCCAG CGCCTGAGCC TCCCTCGGGC TGCACCCTGC CCTGGGTGGG AAAAGGGAAG     269

CAGACAAGAA AAGGGGGCAC AAGGTCACTA CTGTGGGCTG ATGGCCAGTG AACCTGAGCC     329
```

| | | | | | |
|---|---|---|---|---|---|
|CAGAGGGGCC|GGCTCAGCCG|CAAGGTTACA|GGCGCCGAGA|GAACCACCAG|TCGCAGGCCC| 389

CACCCGAAAA CCGTGTCTGT CCCTTCAACA GAG TCA TCG AGG AGG GGT GGC TGC    443
                                 Glu Ser Ser Arg Arg Gly Gly Cys
                                  1               5

TAGCCGTTCT GAGCTCATCC CAGGCCCCTG GGTCTCCGGG TCACTCCCAT TCTGACTGTA   503

CAATCACCAA AAGCCAAGGA GGGCCCGGCA CCCAGCCCAG GGCACAGCTG AGTCTGCGTC   563

CAGCCCAACA CCAGCCCACG GCCTCACTCC CCAGCCTCGG TCTGACCCTT CTAGCCCTGA   623

GATCCAAGTG CCTGGCATCC CCGTCCCCCA AGCCTCACCC AGACCTTCTT TCCCTTCACC   683

CACCCCTCCT GCCACCC                                                 700

( 2 ) INFORMATION FOR SEQ ID NO:5:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

Val Gln Arg Phe Leu Ser Ala Thr Arg Gln Gly Arg Pro Gln Thr Ser
 1               5                  10                  15

Leu Asp Tyr Thr Asn Val Leu Gln Pro His Ala
             20                  25

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Glu Ser Ser Arg Arg Gly Gly Cys
 1               5

( 2 ) INFORMATION FOR SEQ ID NO:7:

( i ) SEQUENCE CHARACTERISTICS:
        ( A ) LENGTH: 136 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Gly Ala Ala Val Pro Leu Ser His Ala Ala Gly Glu Ala Pro Asp Leu
 1               5                  10                  15

Pro Arg Leu His Gln Arg Pro Ala Pro Arg Leu Gly Arg Gly Pro
             20                  25                  30

Leu Thr Leu His Gln Ala Gln Leu Phe Leu Cys Gln Arg Leu Ser Leu
             35                  40                  45

Pro Arg Ala Ala Pro Cys Pro Gly Trp Glu Lys Gly Ser Arg Gln Glu
         50              55                  60

Lys Gly Ala Gln Gly His Tyr Cys Gly Leu Met Ala Ser Glu Pro Glu
 65                  70                  75                  80

Pro Arg Gly Ala Gly Ser Ala Ala Arg Leu Gln Ala Pro Arg Glu Pro
                 85                  90                  95

Pro Val Ala Gly Pro Thr Arg Lys Pro Cys Leu Ser Leu Gln Gln Ser

```
                               100                       105                       110
His  Arg  Gly  Gly  Val  Ala  Ala  Ser  Arg  Ser  Glu  Leu  Ile  Pro  Gly  Pro
          115                      120                      125
Trp  Val  Ser  Gly  Ser  Leu  Pro  Phe
     130                 135
```

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:8:

TCATGCGGTC CACGACCAAG A       21

IGE ISOFORMS AND METHODS OF USE

The research carried out described in the subject application was supported at least in part by grants AI15251, AI115352 (CIRID at UCLA), CA30515 and CA43503 from the National Institutes of Health. The government may have rights in any patent issuing on this application.

INTRODUCTION

1. Technical Field

The field of this invention is IgE isoform-mediated immune hypersensitivity diagnostics and therapeutics.

2. Background

The IgE isotype, defined by the immunoglobulin epsilon heavy chain, plays a complex role in the immune system which includes combating parasitic infections and mediating immediate hypersensitivity allergic reactions. IgE appears to mediate immediate-type hypersensitivity (allergic) reactions including various allergic reactions such as hay fever, extrinsic asthma, and allergies to certain foods, drugs, etc. by virtue of its ability to bind with high affinity epsilon-specific Fc receptors on certain cells such as mast cells and basophils. It appears that the subsequent binding of allergen triggers crosslinking of the bound IgE and their Fc receptors which in turn triggers release of a host of pharmacologic and inflammatory mediators such as histamine and interleukins. Accordingly, while IgE represents only a minute fraction of antibody present in circulation, the concentration of this isotype seems to correlate with some allergic diseases, or at least their severity, and assaying for the presence of allergen-specific IgE is used for diagnosing immediate-type hypersensitivity.

Northern blot analysis of RNA from human myeloma and hybridoma lines secreting Ig other than IgE generally reveal two bands corresponding to transcripts encoding either a membrane-bound or secreted Ig protein. These two RNA species appear to result from alternative splicing which either includes or excludes a sequence encoding a peptide, the "transmembrane sequence", responsible for membrane anchoring. Recent publications report the identification of three mRNA species with IgE membrane exon sequences suggesting a total of four potential human IgE isoforms: the conventional secreted form, two membrane-bound forms, and an additional secreted form.

Relevant Literature

The nucleotide sequence of the murine immunoglobulin epsilon gene is disclosed in Ishida et al. (1982) EMBO J 1, 1117; and the human epsilon constant region locus in Max et at., (1982) Cell 29, 691. IgE isoforms are described in Saxon et at. (1991) J Immunol 147, 4000; Peng et al (1992) J Immunol 148, 129–136; Zhang et al (1992) J Exp Med 176, 233–243; and Hellman (1993) Eur J Immunol 23, 159–167.

SUMMARY OF THE INVENTION

Methods and compositions are provided relating to novel IgE isoforms and their use in immune hypersensitivity diagnosis and treatment. The compositions include transcription and translation products of the immunoglobulin epsilon locus, specific probes for epsilon transcription products, and compounds which specifically bind epitopes of epsilon translation products. Novel products of the epsilon locus include the following transcription products and translation products thereof: CH4-M2"(SEQ ID NO:02residues 1–107 and SEQ ID NO: 06) CH4'-CH5-M1'-M2 (see SEQ ID NO:02, residues 1–72, SEQ ID NO:03 and SEQ ID NO:05), CH4'-CH5-M2' SEQ ID NO:02, residues 1–72, SEQ ID NO:03 and SEQ ID NO:07) and CH4'-CH5-M2"(SEQ ID NO:02, residues 1–72, SEQ ID NO:03 and SEQ ID NO:06). Such epsilon products, specific probes and binding compounds find use in methods and kits for immune hypersensitivity diagnosis and treatment.

BRIEF DESCRIPTION OF THE DRAWINGS

FIG. 1. Epsilon gene nucleotide sequences related to the various alternative splices investigated in this study. The position of these regions (CH4 through M2') are given at the bottom of FIG. 2A.

(A) The genomic sequence of human CH4 (nucleotides 1–323) and its 3' flanking sequence is presented (SEQ ID NO:01) and the amino acid translation for the CH4 domain (see SEQ ID NO:02) and CH4'-CH5 splicing product (see SEQ ID NO:03) is given below the nucleotide sequence. The bold brackets represent donor or acceptor sites of the full length CH4 and the dashed brackets define the boundary of CH4'-CH5 splicing. The oligonucleotides used for primers or probes are also shown; the arrow under the sequence indicates that the oligo was designed based on the strand complementary to that shown here.

(B) Human ε membrane exon 2' (nucleotides 89–498) and its 3' untranslated region sequence is shown (SEQ ID NO:04). The amino acid sequences generated from the various alternative splicing products in different reading frames are also given. The bold brackets define the boundary of the splice acceptor sites described. The amino acid translation shown above nucleotide sequence 89–169 (SEQ ID NO:05) represents the M1'-M2 and M1-M2 splicing products while that from nucleotide position 421 (SEQ ID NO:06) represents the amino acid sequence of the M2" form described in this paper. The amino acid translation shown below nucleotide sequence 89–495 (SEQ ID NO: 07) represents the M2' reading frame. The location of the oligonucleotides used for primers or probes are given as in (1A).

FIG. 2. Analysis of RT-PCR products (amplified with oligonucleotide primers 3 and 9) demonstrating the occurrence of three true PCR products (bands 1, 3 and 5). Aliquots of PCR products were run in 1.5% agarose gels in TBE buffer and a 123 bp ladder was used for DNA size markers. A diagram is provided of CH4 through the 3' untranslated region of M2' showing the location of the nucleotide primers and probes. Circled numbers identify the oligonucleotide probes used in the Southern blots.

Figure 2A:
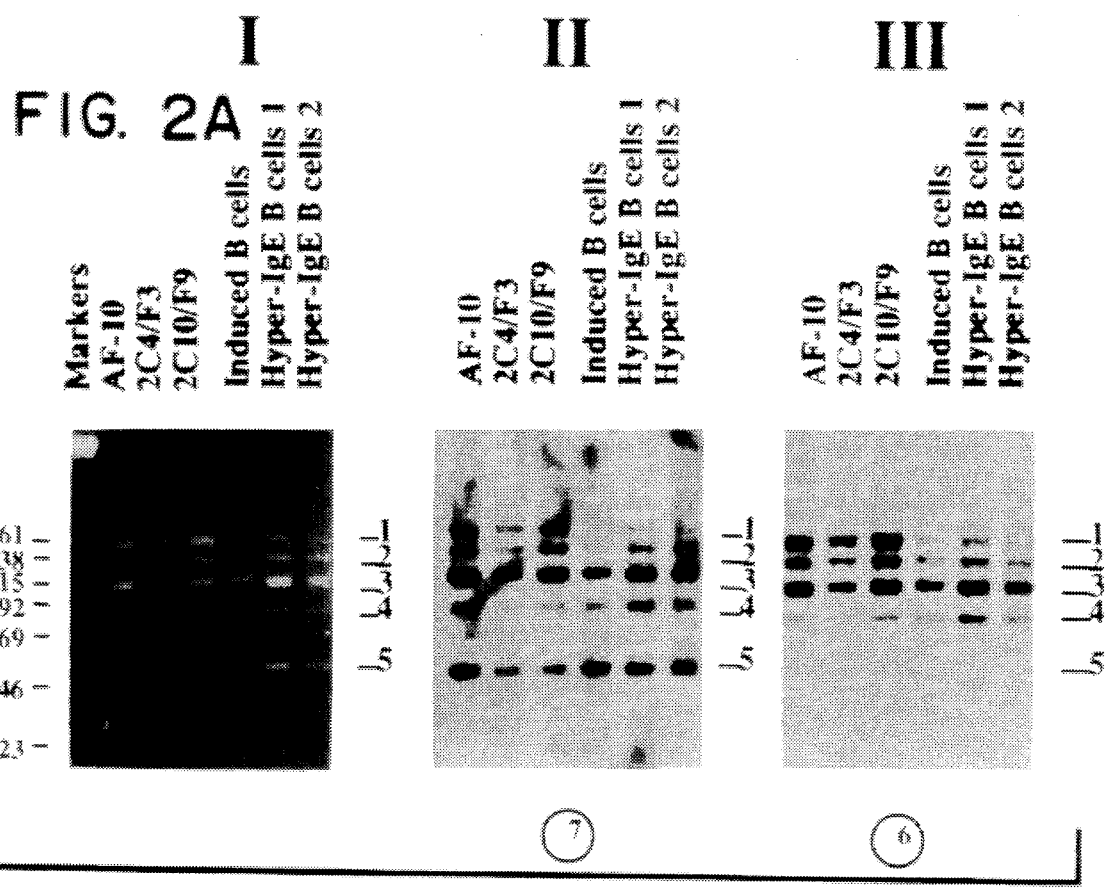

FIG. 2(A) Southern blot analysis of RT-PCR products amplified with primers 3 and 9 from various type of cells. Panel I shows the identical 5 bands are generated from each source of ε mRNA as indicated in the Figure in the ethidium bromide (EB) stained gel. Panel II shows that 5 bands from all the types of cells hybridize to probe 7 indicating that they are carrying the terminal M2' sequence. In panel III, only the larger 4 bands are seen to hybridize with probe 6 indicating that only these bands contain the 5' sequence of M2/M2'.

Figure 2B:
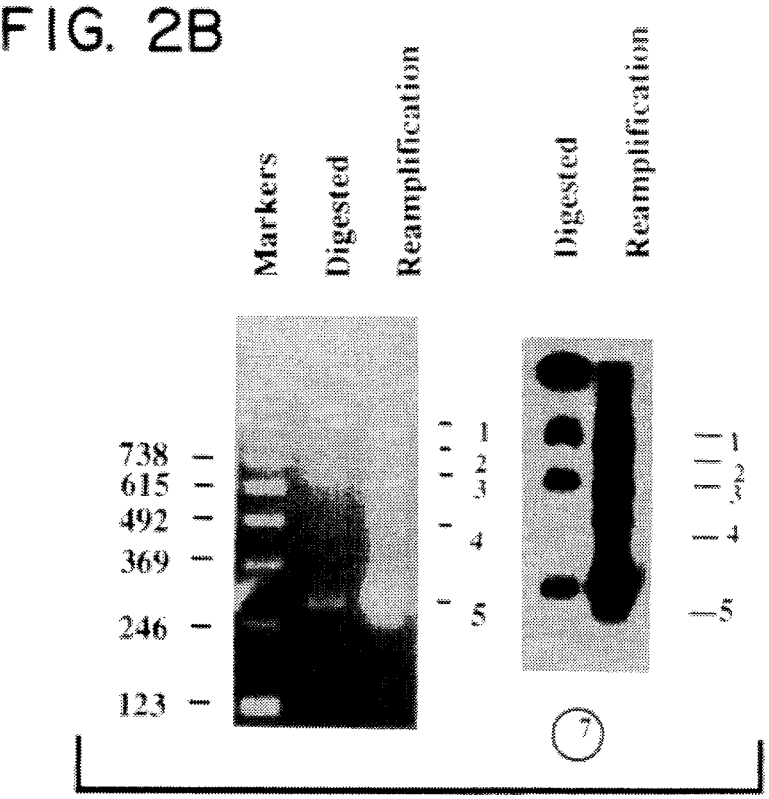

FIG. 2(B) Amplification of a mixture of plasmid vectors containing subclones of band 1, 3 and 5 reconstitute all 5 bands seen on RT-PCR of ε mRNA in FIG. 2A. Plasmid vectors containing subclones of bands 1, 3 and 5 were digested with endonucleases (Cla I and Sal I) and mixed together 0.1 μl of these mixtures, serving as DNA templates, was amplified with primer set 3 and 9. Panel I represents the EB staining results from both digested products showing three true bands and reamplified products showing occurrence of 5 bands; these results demonstrate the production of bands 2 and 4 by in vitro conditions (heteroduplex formation) from the original 3 templates. The slightly slow mobility in the digested band, compared to the corresponding bands in reamplified band, likely results from the presence of cohesive ends generated by endonuclease digestion. Panel II shows that both digested and reamplified products are hybridized to the internal probe (oligo 7) indicating the specificity of these products.

FIG. 3. Gel electrophoresis of RT-PCR products for identifying the existence of CH4'-CH5 splicing. The gel running conditions and DNA markers are the same as in FIG. 2. A diagram is provided of CH4 through the 3' untranslated region of M2' showing the location of the nucleotide primers and probes. Circled numbers identify the two oligonucleotide probes used in the Southern blots.

Figure 3A:
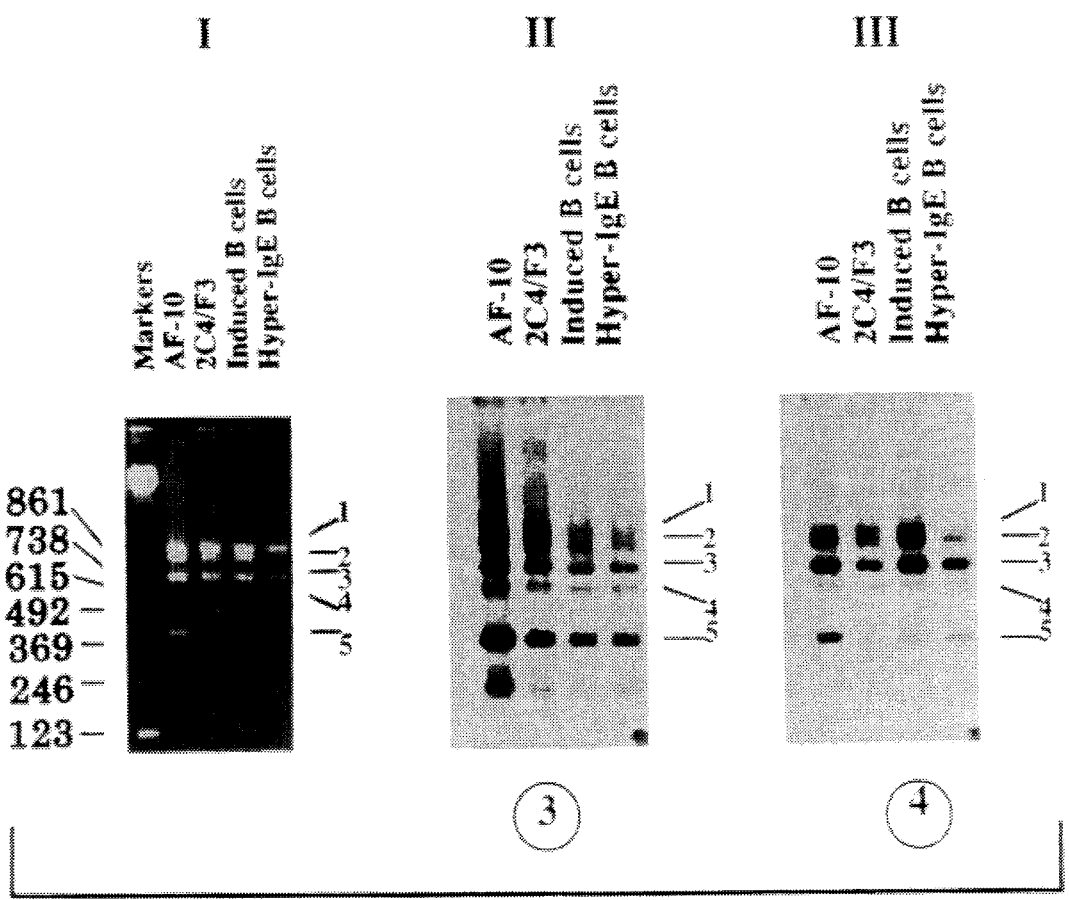

FIG. 3(A) Southern blot analysis of RT-PCR products amplified using primer pair 2 and 9. Panel I is the EB stained gel showing that the similar 5 band pattern is generated from each source of $\epsilon$ mRNA analogous to the pattern seen in FIG. 2A. Panels II and III show hybridization with oligonucleotide probes 3 and 4 respectively; all 5 bands from all cell sources hybridized to oligonucleotide 3 as well as oligonucleotide 4. The presence of sequence hybridizing to probes 4 demonstrates that CH4'-CH5 spliced products are present in the 5 bands observed. However, products not containing this CH4'-CH5 splice exist but are of the same size.

Figure 3B:
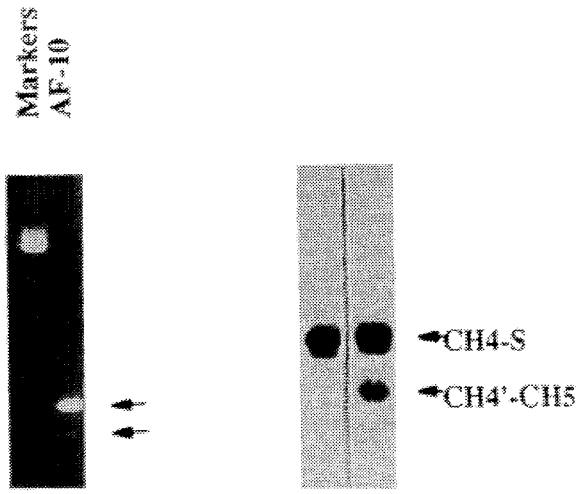

FIG. 3(B) Identification of two PCR products representing CH4-S and CH4'-CH5. Transcripts containing CH4-S versus CH4'-CH5 splicing were amplified as cDNA from AF-10 cells with oligonucleotide primer set 1 and 5. Southern blot analysis with oligonucleotide probes 3 and 4 revealed that a ~450 bp band hybridized only to oligonucleotide probe 4. This demonstrates that the larger product represents RNA transcripts with the full length, like mRNA for the classic secreted epsilon, while the smaller band results from CH4'-CH5 splicing.

Figure 4:
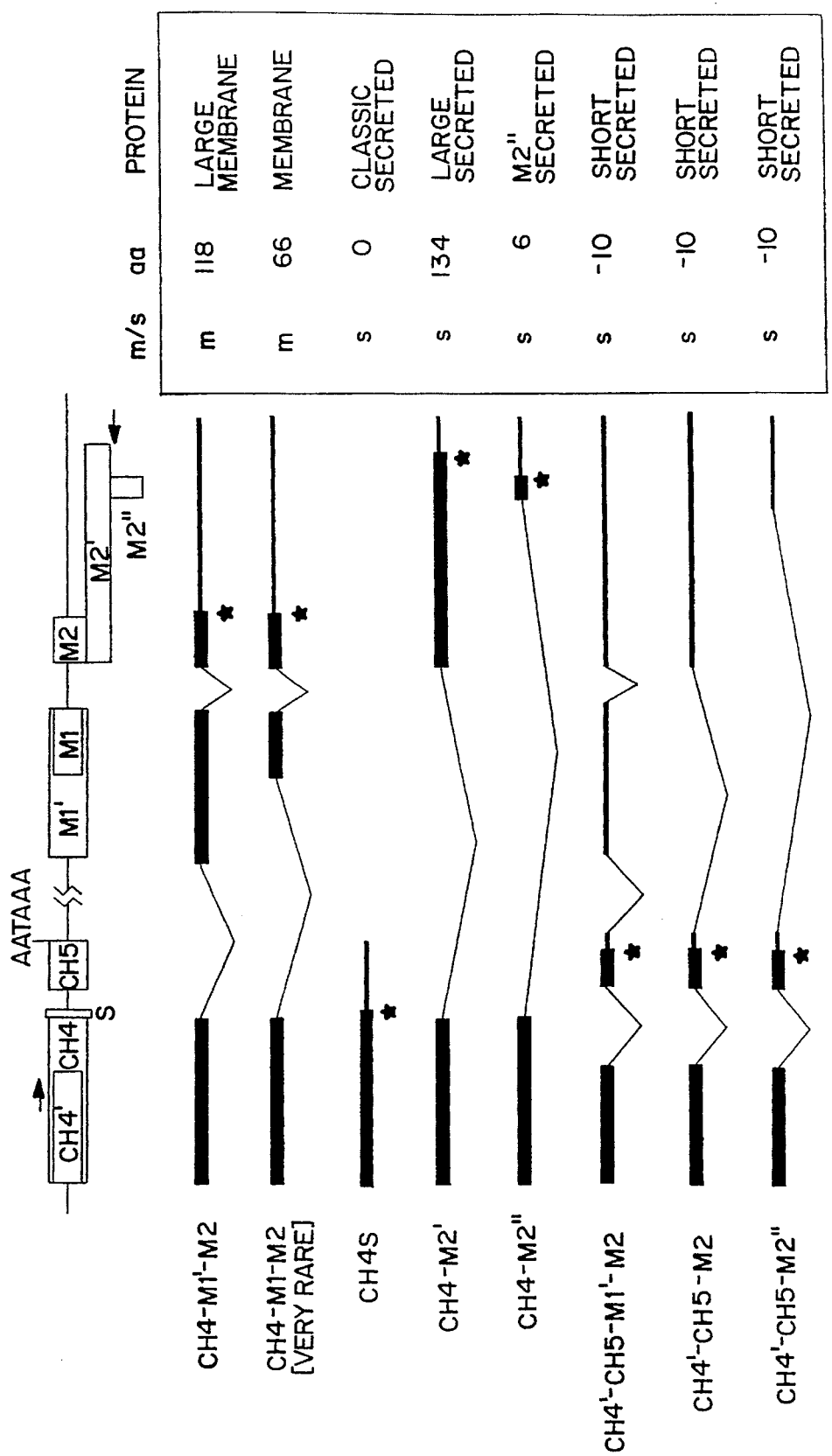

FIG. 4. Diagrammatic summary of 3' ends of $\epsilon$ RNA species. A schematic genomic DNA map for CH4 and the $\epsilon$ membrane exon region sequence is shown at the top. All the sequence confirmed splicing products are shown to the right of their corresponding names and compared with the classic secreted form that is listed on the top. The table at right indicates which forms are membrane (m) vs secreted (s) and shows the number of amino acids longer or shorter than the classical secreted form. The bold horizontal bars represent translated sequence. The asterisks show the position of in-frame termination codons, the thin horizontal lines represent 3' untranslated sequence.

DESCRIPTION OF SPECIFIC EMBODIMENTS

The compositions of the invention include isolated novel IgE heavy chain constant region (epsilon) nucleotide sequences and polypeptides comprising an epitope specific to a translation product encoded by such epsilon nucleotide sequences. Included are novel epsilon exons and novel alternatively spliced transcripts of previously identified epsilon exons. The novel epsilon nucleotide sequences include CH5, a novel epsilon exon, and M2" and CH4' where CH4' is joined to other than CH4", novel alternatively spliced epsilon transcript portions, as described herein or sequences of substantial sequence or structural homology thereto. Substantial sequence homology means that at least 50%, preferably at least 70% and more preferably at least 90% shared sequence identity with the disclosed epsilon sequences. A substantially homologous sequence hybridizes to a disclosed sequence under low stringency conditions, for example, at 50° C. and 6× SSC (0.9M saline/0.09M sodium citrate) and remains bound when subject to washing at 55° C with 1× SSC.

CH4' joined to other than CH4" means that the nucleotide sequence described as CH4' may be joined to any, or no other, nucleotide sequence other than that portion of CH4 downstream (3') of CH4". CH4' is preferably joined to at least a portion of another epsilon nucleotide sequence (except of course, CH4") and more preferably at least a portion of CH5. By joined is meant that the sequences form a continuous polynucleotide sequence though the joined portions may be dispersed by intervening sequences. As will be clear from the figures and following disclosure, the coding sequence of M2" has a reading frame shift as compared with M2'. As used herein, M2" translation products derive from the disclosed M2" reading frame, i.e. the disclosed M2" codon sequence.

An epitope of a translation product is a three-dimensional structural conformation presented by the translation product which distinguishes the translation product from other epsilon translation products. While such epitopes are functionally defined in terms of a spatial conformation, typically, such epitopes are identified by amino acid sequence homology with the disclosed sequences or with antibodies, preferably monoclonal antibodies, which are capable of distinguishing one epsilon translation product from other epsilon translation products. Specific binding to such an epitope is conveniently shown by generally known solid phase or competitive binding assays. Specific binding will generally have a binding affinity of $10^{-6}$M, preferably $10^{-8}$M and more preferably $10^{-10}$M under optimized conditions and temperature.

The polypeptides of the invention include peptide sequence encoded by novel epsilon nucleotide sequences, are generally at least about 8 amino acids in length, preferably at least 20 amino acids in length and preferably less than about 1,000 amino acids. In addition to an epitope of an epsilon translation product, the polypeptides will frequently include most or all of a polypeptide epitope encoded by an epsilon nucleotide sequence and may comprise up to an entire IgE immunoglobulin or complex containing IgE. In addition, the polypeptides may be fused, for instance by recombinant, enzymatic, or chemical methods, to other chemical groups such as saccharides, lipids, peptides or polypeptide domains. Useful fusion partners include labels, cytotoxins, cytokines such as lymphokines, drugs such as immunosuppressive agents and molecules to enhance stability when used in culture or in vivo, to ease transport across membranes, to direct the epsilon encoded domain(s) to a particular site or cell type, for ease of administration, or to modulate the binding characteristics.

An isolated polypeptide or nucleic acid is unaccompanied by at least some of the material with which it is associated in its natural state. Generally, an isolated polypeptide constitutes at least about 1%, preferably at least about 10%, and more preferably at least about 50% by weight of the total protein in a given sample. Included in the polypeptide weight are alternative forms such as differentially glycosylated or phosphorylated or otherwise post-translationally modified forms. By pure polypeptide is intended at least about 90%, preferably at least 95%, and most preferably at least about 99% by weight of protein.

An isolated nucleic acid sequence is present as other than a naturally occurring chromosome or transcript in its natural state and typically is removed from at least some of the nucleotide sequences with which it is normally associated with on a natural chromosome. A partially pure nucleotide sequence constitutes at least about 5%, preferably at least about 50%, and more preferably at least about 90% by weight of total nucleic acid present in a given fraction. The nucleic acids of the invention, other than those used in PCR amplification, are usually at least about 60 bp and usually less than about 6 kb in length. The PCR primers are generally between about 5 and 1K nucleotides, and preferably between about 10 and 100 nucleotides in length.

The invention provides for epsilon nucleic acid sequences and such sequences modified by transitions, transversions, deletions, insertions, or other modifications, genomic sequences, flanking sequences, including regulatory and other non-transcribed sequences of the disclosed epsilon sequences, RNA and DNA antisense sequences complementary to the disclosed epsilon sequences, sequences encoding xenogeneic homologs of the disclosed sequences and sequences comprising synthetic nucleotides. Typically, the invention's epsilon sequences are associated with heterologous sequences such as regulatory sequences, e.g. promoters, enhancers, response elements, signal sequences, polyadenylations sequences, etc., introns, noncoding regions, etc. The sequences may be modified with a label providing form identification and/or isolation. Exemplary labels include radioisotopes, fluorescers, biotinylation, etc.

The invention provides vectors comprising the disclosed nucleic acids. A large number of vectors, including plasmid and viral vectors, have been described for expression in a variety of eukaryotic and prokaryotic hosts. Vectors will often include one or more replication systems, one or more markers for selection in the host, e.g. antibiotic resistance, and one or more expression cassettes. The inserted epsilon sequences may be synthesized, isolated from natural sources, prepared as hybrids, etc. Ligation of the coding sequences to the transcriptional regulatory sequences may be achieved by known methods. Advantageously, vectors may also include a promotor operably linked to an epsilon peptide encoding nucleic acid sequences.

Suitable host cells may be transformed/transfected/infected by any suitable method including electropotation, $CaCl_2$ mediated DNA uptake, viral infection, microinjection, microprojectile, or other established methods. Alternatively, nucleic acids encoding one or more epsilon polypeptides may be introduced into cells by recombination events. For example, a sequence can be microinjected into a cell, and thereby effect homologous recombination at the site of an endogenous gene comprising an epsilon sequence, an analog or pseudogene thereof, or a sequence with substantial identity to an epsilon sequence. Other recombination-based methods such as nonhomologous recombinations, deletion of endogenous gene by homologous recombination, especially in pluripotent cells, etc., provide additional applications.

Appropriate host cells include bacteria, archebacteria, fungi, especially yeast, and plant and animal cells, especially mammalian cells. Of particular interest are *E. coli, B. subtilis, Saccharomyces cerevisiae,* SF9 and SF21 cells, C129 cells, 293 cells, Neurospora, and CHO, COS, HeLa cells and immortalized mammalian myeloid and lymphoid cell lines. Useful replication systems include M13, ColE1, SV40, baculovirus, vaccinia, lambda, adenovirus, AAV, and BPV. A large number of transcription initiation and termination regulatory elements/regions have been isolated and shown to be effective in the transcription and translation of heterologous proteins in the various hosts. Examples of these regions, methods of isolation, manner of manipulation, etc. are known in the art. The particular choice of vector/host cell is not critical to the invention. Under appropriate expression conditions, host cells are used as a source of recombinantly produced epsilon sequences. Preferred expression systems include *E. coli,* vaccinia virus, or baculovirus; the latter two permitting the recombinant epsilon sequences to be modified, processed and transported within a eukaryotic system.

Epsilon oligonucleotides are also used to identify other immunoglobulin epsilon sequences. For example, the disclosed nucleic acids are labeled and used to screen cDNA libraries at low stringency to identify similar cDNAs that encode proteins with related domains. Additionally, related immunoglobulin domains are isolated by PCR amplification primers as described herein or degenerate oligonucleotide probes derived from epsilon peptide sequences. PCR primers are generally between 4 and 1000 bp, prefereably between 6 and 100 bp, more preferably between 10 and 50 bp in length and primer pairs usually separated by less than about 2 kb. Other useful cloning, expression, and genetic manipulation techniques for practicing the inventions disclosed herein are described in the following exemplification or are otherwise known to those skilled in the art and familiar with the methods herein or found in standard manuals such as Molecular Cloning, A Laboratory Manual (2nd Ed., Sambrook, Fritsch and Maniatis, Cold Spring Harbor), Current Protocols in Molecular Biology (Eds. Ausubel, Brent, Kingston, Moore, Seidman, Smith and Struhl, Greene Publ. Assoc., Wiley-Interscience, New York, N.Y., 1992).

The invention provides a wide variety of compounds and agents which specifically bind a translation product of the disclosed sequences. Typically, such compounds and agents are identified by screening large numbers of compounds for specific binding to the disclosed epsilon encoded epitopes. The invention also provides for compounds or agents which are capable of influencing the relative transcription or translation of the IgE isoforms disclosed herein. These regulatory agents are identified by cell-based in vitro assays of isoform transcription or translation. Such agents provide pharmaceuticals for modulating the IgE isoform expression of a host.

Typically, prospective agents are screened from libraries of synthetic or natural compounds. For example, numerous means are available for random and directed synthesis of saccharide, peptide, and nucleic acid based compounds, see, e.g. Lam et at., (1991) Nature 354, 82–86. Alternatively, libraries of natural compounds in the form of bacterial, fungal, plant and animal extracts are available or readily producible. Additionally, natural and synthetically produced libraries and compounds are readily modified through conventional chemical, physical, and biochemical means.

Useful agents are found within numerous chemical classes, though typically they are organic compounds; preferably small organic compounds. Small organic compounds have a molecular weight of more than 50 yet less than about 2,500, preferably less than about 500. Exemplary classes include peptides, saccharides, steroids, and the like. Selected agents may be modified to enhance efficacy, stability, pharmaceutical compatibility, and the like.

Other useful epsilon peptide specific binding compounds include IgE isoform specific binding proteins. As discussed below, cellular responses usually distinguish IgE isoforms on the basis of differential binding to cellular proteins such as Fc receptors and other IgE binding proteins. Thus the isoforms and peptides disclosed herein are used to affinity purify a variety of cellular and serum IgE binding proteins. Such IgE binding proteins in turn find use as agents for modulating immune responses. Methods for affinity purifying IgE binding proteins are known in the art or otherwise disclosed or referenced herein.

Specific polyclonal or monoclonal antibodies that specifically bind the disclosed epsilon encoded epitopes are conveniently made using the compositions disclosed herein. For example, immunogenic peptides according to the sequences disclosed herein are conveniently made by chemical synthesis, recombinant techniques, biosynthesized, etc. Preferred peptides are readily identified from the sequences disclosed herein using techniques such as hydrophobicity plots as described in Zhang et al (1992). These peptides may be conjugated to a variety of carriers such as KLH, etc. Accordingly, antibodies which specifically recognize each IgE isoform are provided. Detailed methods for making specific antibodies, immunization protocols, monoclonal antibodies, etc are found in Harlow and Lane, Antibodies, A Laboratory Manual, Cold Spring Harbor Laboratory, 1988, other references cited herein, as well as immunological and hybridoma technologies known to those in the art.

The expression of IgE isoforms and transcripts thereof disclosed herein provide biochemical and ultimately biological consequences. For example, the replacement of CH4" with CH5 creates an unusual immunoglobulin domain that only has one cysteine residue. Accordingly, the normal intramolecular disulfide bonding characteristic of previously characterized Ig is not possible. Similarly, isoforms containing the disclosed M2" sequence generally have a terminal cysteine residue. Consequently, this isoform demonstrates differential propensities toward forming homo- and heterodimer and multimers through disulfide linkages with the terminal cysteine residue. Such structural consequences in turn provide CH5 and M2" containing IgE isoforms with differential ability to bind Fc receptors and participate in immune-sensitivity responses.

Additionally, the isoforms disclosed herein present disparate targets for posttranslational modifications such as phosphorylation and glycosylation. For example, some isoforms differ in their glycosylation patterns, in turn providing for differential binding to ligand-like IgE binding proteins (See e.g. Biochemistry (1990), 29, 8093–8100). Through their differential ability to bind other cellular components, the isoforms disclosed herein provide disparate ability to mediate a broad range of biochemical and cellular responses.

In addition, the epsilon transcripts disclosed herein also provide functional distinctions. For example, three structurally distinct transcripts are disclosed which nevertheless provide for the same peptide coding sequence. The different messages provide variations for example in nuclear translocation, stability, transcription product localization, etc. In turn, differences in mRNA stability provide for expression efficiency by variations in translation product copy number and differential localizations provide for differential access to posttranslational modification enzymes and cellular export machinery.

Accordingly, the epsilon transcription and translation products disclosed herein provide convenient targets for modifying IgE-mediated cellular and physiological function. More specifically, since the differential expression of the disclosed epsilon sequences relates to IgE-mediated immune hypersensitivity conditions and propensity, epsilon-encoded epitope-specific compounds/agents and nucleic acids encoding epsilon encoded epitopes and probes thereto find use in diagnosing and treating such conditions.

Suitable hosts include human, pets such as dogs, cats, rabbits, exotic birds, etc., and farm animals such as horses. Specimens may be biological fluids, tissues, cells, or fractions/preparations thereof. Preferred specimens are derived from blood and include whole blood and fractions thereof including cellular fractions, serum, plasma, etc. Specimens may be treated or prepared in a variety of ways, e.g. blood-derived specimens may be treated with anti-coagulants such as heparin and are commonly diluted with a buffered medium.

For diagnostic uses, host specimens are screened for the presence of one or more epsilon transcription or translation products both as total amount of the specific product (i.e. total circulating M2" IgE) or as amount of antigen-specific IgE isoform (e.g. amount of M2"-IgE against ragweed). Diagnosis is premised on the identification of polypeptides comprising an epitope of a translation product of an epsilon sequence described herein or transcripts encoding such an epitope. Employing the invention's epsilon translation product-specific compounds, specimens may be classed in terms of the IgE isoforms reflected by the identified epitopes of epsilon translation products. Thus, the relative concentrations of the various IgE isoforms (total and antigen specific) in a specimen are determined. Where clinical correlates are not yet established, panels of isoform profiles are readily used to demonstrate correlations to physiological conditions such as immune hypersensitivity, immune disease, tolerance, etc. that are used in subsequent diagnosis. Antigen-specific isoforms are generally assayed by contacting a specimen with suspect allergen/antigen and identifying IgE-allergen/antigen complexes, e.g. by ELISA.

A wide variety of techniques may be used for assaying the epsilon isoform compositions of a specimen with specific compounds. In a preferred embodiment, antibodies specific for given epsilon encoded epitopes are used in otherwise conventional immunoassays for measuring isoforms in a sample. Diagnosis may also encompass ascertaining the specificity of the isoform classes. For example, the diagnostic antibodies described above are used to separate the various IgE isoform classes according to conventional affinity binding methods. Thus, effector allergen specific isoforms can be identified.

The relative proportions of various cell types bearing particular isoforms can also be determined. For example, many IgE isoforms comprising the epsilon encoded translation products described herein will be secreted forms, lacking membrane anchoring domains. These isoforms present differential abilities to bind to cellular Fc receptors and IgE binding proteins. When cellular bound, the isoforms are used to identify and hence permit targeting of, or selection/separation of, cells bearing epsilon specific Fc receptors, or specific classes thereof. Such cell types include macrophages, mast cells, basophils and activated T cells. The epsilon epitope-specific antibodies also find use in quantifying and determining the relative proportions of B cells bearing particular isoforms, usually transmembrane isoforms.

Such cellular profiles can help characterize the allergic status of the individual. The method generally entails contacting specific antibodies with a host specimen including leukocytes to be tested under conditions which permit the antibodies to bind IgE-bearing cells in the specimen. Subsequently, the cells are examined for antibody binding, by for example, immunofluorescence. Accordingly, the methods and compositions disclosed herein provide for profiling soluble, transmembrane, and Fc bound IgE isoforms, IgE isoform-specific Fc receptors, and cell types bearing various IgE isoform-specific Fc receptors.

Alternatively, diagnosis can be obtained by using various hybridization-based techniques such as PCR and Northern blotting to identify epsilon transcripts. Suitable techniques for PCR amplification of the epsilon transcripts of the invention are set out in the exemplification below or references cited herein. Of particular interest are primer pairs that specifically amplify the novel epsilon exons and spliced products disclosed herein. More particularly preferred are primers which are substantially homologous with epsilon exon splicing junctions. By junctions is meant the nucleotide sequences immediately up and downstream of the splice sites. Generally, junctions comprise at least 3 and preferably at least 4 nucleotides on one side and at least one and preferably at least 2 nucleotides on the other side of a splice site. For example, primers of at least a portion of which overlap the CH4'-CH5 and the CH4-M2"junctions can be used to amplify and identify mRNA molecules containing these splice cites. By primer portion is meant at least about 4, preferably at least about 6 nucleotides of a primer. By overlap is meant that the primer and target site are sufficiently complementary that primer hybridization is specific enough to amplify the target sequences within standard PCR reaction conditions. Typically, the hybridizing primer portion and homologous strand are at least about 80% identical.

Accordingly, by selecting primers for specific exon amplification and employing a series of PCR reactions or by using multiple sets of primers simultaneously, convenient analysis of the epsilon exon profile of a specimen is provided. Additional protocols for Northern blot hybridizations and PCR reactions may be found in standard manuals such as Molecular Cloning, A Laboratory Manual (2nd Ed., Sambrook, Fritsch and Maniatis, Cold Spring Harbor), Current Protocols in Molecular Biology (Eds. Ausubel, Brent, Kingston, Moore, Seidman, Smith and Struhl, Greene Publ. Assoc., Wiley-Interscience, N.Y., N.Y., 1992).

The methods and compositions herein also find use therapeutically in the treatment of IgE-mediated hypersensitivity. The epsilon epitope-specific compound/agents (e.g. antibodies) may be used as immune function effector agents, as carriers for drugs, cytokines, cytotoxic agents, etc. For example, the cytotoxic antibody conjugates may be used to reduce or eliminate certain IgE-bearing cells by cytolysis or other regulatory immune mechanisms.

Where antibodies are administered therapeutically, it is desirable to minimize the likelihood of an immunogenic or allergenic response by using human antibodies, chimeric antibodies, human expression vectors to produce fragments of human antibodies or antibodies wherein only the antigen combining site is non-human. While intact antibodies are commonly used, the antibodies may be modified in a variety of ways, by enzymatic cleavage to provide fragments, reduction of disulfide linkages, and the like. Antibody therapy may also be used in conjunction with conventional desensitization immunotherapy or enhanced with factors that augment ADCC activities such as GM-CSF or M-CSF.

In additions, polypeptides comprising epsilon-encoded epitopes themselves find therapeutic use. Peptides thereof may be used to interfere with hypersensitivity reactions and onsets thereof. For example, classes of epsilon-specific Fc receptors on certain mast cells and basophils can be blocked with non-crosslinking compounds and prevent allergic reaction. Such treatments may be administered prophylactically or, especially in cases of anaphylaxis, acutely.

For therapeutic uses, the compositions and selected agents disclosed herein may be administered by any convenient way that will depend upon the nature of the compound/agent, the purpose and frequency of the treatment. For small molecular weight agents, oral administration is preferred and enteric coatings may be indicated where the compound is not expected to retain activity after exposure to the stomach environment. Generally the amount administered will be empirically determined, typically in the range of about 0.1 to 1000 ug/kg of recipient.

Large proteins are preferably administered parenterally or systemically, conveniently in a physiologically acceptable carrier, e.g., phosphate buffered saline, saline, deionized water, or the like. Some agents, such as antibodies can also be administered nasally. Typically, compositions are added to a retained physiological fluid such as blood. Generally, the amount administered will be empirically determined, typically in the range of about 10 to 1000/μg/kg of the recipient. Other additives may be included, such as stabilizers, bactericides, etc. These additives will be present in conventional amounts.

The invention provides for diagnostic kits for obtaining IgE isoform and IgE isoform-specific Fc receptor profiles for hypersensitivity or allergy testing. These kits may include containers, e.g. microtiter plates. In one type of kit the container walls are pre-coated with a first IgG class antibody specific for one or more IgE isoforms. In a second kit, prospective allergen(s) is/are immobilized, preferably on the surface of a multi-well plate. In both cases, a separately packaged second, preferably polyclonal, antibody conjugated to a label and specific to one or more IgE epitopes is provided. Where enzyme-labelled antibody is provided, substrate and reaction stopping reagents may also be provided.

Alternative kits are based on the identification of mRNA species amplifiable by PCR from a specimen. Preferred primers are substantially homologous to mRNA regions which overlap two epsilon exons or alternatively spliced exon portions such as the CH4'-CH5 junction and the CH4-M2" junctions. A preferred kit contains sufficient primers to simultaneously amplify any of all the diagnostically useful epsilon exons from a specimen. Other useful junctions include CH4-M1', CH4-M2", M1-M2, M1'-M2, CH3-CH5, CH5 joined to the various M regions, etc.

The following examples are offered by way of illustration and not by way of limitation.

EXPERIMENTAL

Materials and Methods

Cell lines and cell cultures.

The human IgE secreting cell line AF-10 cells was maintained in complete RPMI 1640 medium as described previously in Saxon, et al., 1991, *J. Immunol.* 147:4000. EBV transformed IL-4-induced IgE-secreting human B cell lines 2C4/F3 and 2C10/F9 (described in Thyphronitis, et al., 1991, *J. Immunol.* 146(5):1496) were maintained in complete RPMI 1640 supplemented with 50 mM Hepes and $3\times10^5$M 2-mercaptoethanol (Sigma). Fresh purified human B cells were isolated from tonsil and purified by the methods described previously in Saxon et al., 1976, *J Immunol Methods*, 12:285. For induction of productive ε transcripts, purified B cells ($1\times10^6$ cell/ml) were cultured for 7 days in the presence or absence of 100 U/ml recombinant IL-4 plus 0.1 μg/ml of anti-CD40 mAb G28-5 (See Zhang et al., 1991, J Immunol., 146(6):1836). Spontaneously IgE producing human B cells were obtained from patients with the Hyper-IgE immunodeficiency syndrome or atopic dermatitis.

Amplification.

RNA was isolated from the various cells and reverse transcribed by standard methods as described by Zhang et al., 1992, *J. Exp. Med.* 176:233. Pairs of PCR primers were designed to detect different forms of ε mRNA containing membrane exon sequences (Table 1 and: FIGS. 1(A) and 2(B)). The same primer used by Zhang et al., 1992, was used in the present work but is referred to by a different name herein. The primer is listed under both names in Table 1. Some primers were designed with terminal enzyme restriction sites to facilitate cloning and sequencing of PCR products. PCR amplifications were performed for 40 cycles under the conditions described in Zhang et al., 1992.

Southern blot analysis of PCR products.

PCR products were electrophoresed on 1.5% agarose gels. DNA was transferred to nylon membranes (Nytran, Schleicher & Schuell Inc., Keene, N. H.) in 0.4M NaOH. Blots were analyzed by probing with end-labelled oligonucleotides corresponding to various regions of the genomic sequence shown in FIGS. 1(A) and 2(B). Hybridization with kinased oligonucleotide probes was performed as described in Zhang et al., 1992.

Analysis of amplified ε cDNAs.

PCR products were digested with Cla I and Sal I, purified by agarose gel electrophoresis, and then ligated into Bluescript® (Stratagene, La Jolla, Calif.) vector that had been prepared by Cla I and Sat I digestion and treatment with alkaline phosphatase. Plasmid minipreps were analyzed by restriction digestion, agarose gel electrophoresis and hybridization to internal probes. The inserts of the selected clones were sequenced on both strands by the dideoxy termination method using a sequencing kit purchased from USB (USB, Cleveland, Ohio).

Results

Splicing of CH4 to a novel splice acceptor site inside the M2' exon.

To explain the multiple IgE bands appearing on Western blots of secreted human IgE, we considered the possibility that splicing of ε immunoglobulin heavy chain RNAs might be more complex than previously described. In our earlier RT-PCR studies of alternative ε RNA splicing we had observed a small DNA fragment that we had considered a possible PCR artifact since it did not hybridize to several probes internal to the exons M1 or M2 (Zhang et at., 1992, FIG. 2, panel D). To explore the possibility that this band reflected a genuine splice form containing sequence downstream from the previously tested M2 probes, we subjected RNA from the IgE secreting cell line AF-10 to RT-PCR using the primer pair 3–9 (Table 1 and FIGS. 1(A) and 1(B)), and included a far downstream probe in our hybridization analysis. Amplifications with this primer pair consistently generated five bands with RNA derived from all IgE+ cells tested. As shown in FIG. 2A, all five of these products hybridized to a probe located downstream of the M2' exon (oligo 7, Table 1), but only the larger (upper) four bands hybridized to an M2' internal probe located in the beginning of the M2' exon (oligo 6, Table 1). These results suggested that one form of ε mRNA, represented by band 5, resulted from splicing to a novel acceptor site inside the M2' exon between oligo 6 and 7.

Because PCR-generated heteroduplex formation between alternative spliced products may cause artifactual bands (Zhang et at., 1992), we investigated whether any of the observed bands represented heteroduplexes. When DNA corresponding to bands 2 and 4 was recovered and subcloned, DNA from band 2 always gave subclones identical to band 1 and band 3, while band 4 always gave subclones identical to bands 3 and 5. No subclones with inserts the size of band 2 or 4 were ever obtained in three experiments. On the other hand, band 2 and band 4 could be generated on gels by reamplifying the DNA templates from mixtures of the subcloned band 1, 3 and 5 (see FIG. 2B). Amplification of templates corresponding to a single subclone never produced band 2 or 4. These experiments indicated that bands 1, 3 and 5 represent true individual PCR products, while bands 2 and 4 are PCR-generated heteroduplexes.

Of the three true PCR products amplified with primer pair 3 and 9, bands 1 and 3 had the correct size and hybridization characteristics expected for two RNA splice forms that we previously described: CH4-M1–M2 and CH4-M2', respectively. These identities were confirmed by sequence analysis. Sequencing further showed that the band 5 products from RNAs derived from all of our IgE+ cells were identical, reflecting an RNA spliced from the usual donor site near the 3' end of CH4 to a novel acceptor site in the terminal portion of the M2' exon (nucleotide 421 in FIG. 1B). The sequence at this position is a typical splice acceptor site. This novel spliced RNA (designated CH4-M2") has a one nucleotide reading frame shift compared with the frame of the same DNA sequence in the previously described CH4-M2' form. As a result, translation of the new CH4-M2" mRNA should terminate at the TAG at position 444 of FIG. 1B. The protein encoded by this RNA would be secreted (as it lacks the membrane anchor sequence of the M1 exon), and in its structure the two C-terminal acids of the "classical" secreted form would be replaced with a novel eight residue C-terminus (FIG. 1B).

Three novel ε RNA transcripts that define a new exon: CH5.

In our previous analysis of ε RNA isoforms, we described a single RT-PCR subclone representing an RNA that spliced from a novel donor site within CH4 (nucleotide 218 in FIG. 1A) to a novel splice acceptor site located in the 3' untranslated region sequence downstream of CH4 (nucleotide 359 of FIG. 1A). This clone, whose structure was designated CH4'-I-M1'-M2 (Zhang et al., 1992), was originally isolated from the same PCR band as the abundant CH4-M1'-M2 splice product. The existence of two PCR products in the same band was explained by the nearly identical sizes of these two products, as the length of the segment designated "I" (107 bp) almost exactly compensates for the DNA lost from the 3' end of the truncated CH4' (106 bp). Our current evidence (described below) indicates that this novel splice is found in all IgE+ cell samples tested, defining a new exon which we have renamed CH5 (to avoid confusion with the "I" exon upstream of the ε switch region).

To investigate RNA forms with this splice, amplification products obtained using the 2(IVm)-9 primer pair were analyzed by Southern blotting and hybridization with oligonucleotide probes specific either for CH5 (probe 4) or for the 3' end of CH4—which is absent from CH4'—(probe 3). Since the IVm primer sequence is 5' to the splice donor site at the 3' end of CH4', this primer should amplify RNA forms with an intact CH4 exon as well as the CH4'-CH5 RNAs (which could not have been amplified by the 3–9 primer pair used in the experiments of FIG. 2). As in the amplification described above, three major bands were produced (labelled 1, 3 and 5 in FIG. 3), along with intermediate-sized bands that appear to be heteroduplex artifacts on the basis of experiments similar to those described above. Strikingly, all five bands hybridized to both probe 3 and probe 4, suggesting that each band might represent a mixture of CH4 and CH4'-CH5 amplification products. This interpretation was supported by cloning the PCR bands 1, 3 and 5; each band yielded some clones hybridizing to probe 3 and others hybridizing to probe 4, but no clones were obtained that hybridized to both probes. Sequence analysis of representative clones containing CH5 showed that this exon always terminated with the same 5' and 3' ends, and that the sequences downstream of CH5 reflected the same three splice acceptor sites observed in the RNA forms that contain intact CH4 and no CH5. These CH5-containing clones thus defined three new RNA splice forms: CH4'-CH5-M1'-M2 (band 1), CH4'-CH5-M2' (band 3) and CH4'-CH5-M2" (band 5). All of these would encode the same protein, because translation of all would terminate within CH5 at the TAA codon at position 440 of FIG. 1A. Clones hybridizing to probe 3 were shown by sequence analysis to reflect the intact CH4 exon spliced to the same three downstream splice acceptor sites, representing splice forms reported earlier (CH4-M1'-M2 and CH4-M2') or described above (CH4- probe for both CH4 and CH4' (oligo 2), but only the larger band hybridized to oligo 3.

It is evident from the above results, that novel epsilon exon or epislon sequences, transcripts, and translation products have been identified. These products and products derivable therefrom find use in diagnosis, therapy, and drug identification.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

TABLE 1

Oligonucleotide sequence of primers and probes employed

| Number | Sequence (5' to 3')* | Position |
|---|---|---|
| 1 | TCATGCGGTCCACGACCAAGA | 3' end of CHe3 domain (Seq. ID No: 08) |
| 2(IVm)** | ggccatcoatGACGCCCGGCACAGCACGACGCAG | 147–170 B17 (FIG. 1a) |
| 3 | ggccatcoatAGGCAGCGAGCCCCTTCACAGACCG | 274–297 B18 (FIG. 1a) |
| 4 | ggccatcoatGAGGACTGGCCAGACCTTCTG | 383–403 B19 (FIG. 1a) |
| 5 | GTCATTGCAACAGTGGACAG | 420–401 B20 (FIG. 1a) |
| 6 | TGCAGCGGTTCCTCTCAGCC | 90–109 B21 (FIG. 1b) |
| 7 | GAATGGGAGTGACCCGGAGAC | 495–475 B22 (FIG. 1b) |
| 8 | ggccgtcgacGACGGGGATGCCAGGCAGTTGGATC | 648–624 B23 (FIG. 1b) |

*Capital letters correspiond to genomic sequence while lower case letters represent added uncleotides.
Underlined sequences represent introduced restriction sites for Cla I (atcgat) or Sal I (gtcgac).
**Oligo 2 is the same primer as IVm in ref (3)

TABLE 2

Splicing donor and acceptor sites utilized in the defined ε mRNA isoforms.

| splicing donor sites consensus (G/GT) | splicing acceptor sites consensus (CAG/) | possible splicing | observed splicing |
|---|---|---|---|
| 3'CH4' GGT | 5'CH5 CAGGG | CH4'—CH5—M1'—M2 | yes |
| 3'CH4 GGT | 5'M1' CAGGG | CH4'—CH5—M1—M2 | no |
| 3'CH5 GGT | 5'M1 CAGAG | CH4'—CH5—M2' | yes |
| 3'M1' GGT | 5'M2 CAGGG | CH4'—CH5—M2" | yes |
| | 5'M2" CAGAG | CH4'—M1'—M2 | no |
| | | CH4'—M2' | no |
| | | CH4'—M2" | no |
| | | CH4—CH5—M1'—M2 | no |
| | | CH4—CH5—M2' | no |
| | | CH4—CH5—M2" | no |
| | | CH4—M1'—M2 | yes |
| | | CH4—M1—M2 | yes |
| | | CH4—M2' | yes |
| | | CH4—M2" | yes |
| | | CH4'—CH5—M1'—M2" | no |
| | | CH4—M1'—M2" | no |

M2"). (Neither the rare CH4-M1-M2 form (3,4) nor a CH4'-CH5'-M1-M2 counterpart was observed in these experiments; nor did we detect any products splicing from the donor site at the 3' end of M1 or M1' to M2".) The existence of the CH4'-CH5 product is still further confirmed by amplification of cDNA with the primer set 1 and 5, a set primers that are able to simultaneously amplify the both constitutive CH4S product (where S states for secreted terminus) and the alternatively spliced CH4'-CH5 products (FIG. 3B). FIG. 3B demonstrates that indeed both predicted PCR products were observed and hybridized to an internal

What is claimed is:

1. An isolated DNA comprising a nucleotide sequence selected from the group consisting of:

CH4' (SEQ ID NO:1, 3–217) spliced to CH5 (SEQ ID NO:1, 359–440); and CH4 (SEQ ID NO:1, 3–323) spliced to M2" (SEQ ID NO:4, 420–443).

2. An isolated DNA consisting of the nucleotide sequence of an exon selected from the group consisting of:

CH4' (SEQ ID NO:1, 3–217);
    CH5 (SEQ ID NO:1, 359–440); and
    M2" (SEQ ID NO:4, 420–443).

3. An isolated DNA selected from the group consisting of:

CH4' (SEQ ID NO:1, residues 3–217) spliced to CH5 (SEQ ID NO:1, 359–440); and
    CH4 (SEQ ID NO:1, 3–323) spliced to M2" (SEQ ID NO:4, 420–443).

4. An isolated DNA according to claim 3, wherein said DNA consists of CH4' (SEQ ID NO:1, residues 3–217) spliced to CH5 (SEQ ID NO:1, 359–440).

5. An isolated DNA according to claim 3, wherein said DNA consists of CH4 (SEQ ID NO:1, 3–323) spliced to M2" (SEQ ID NO:4, 420–443).

6. An isolated DNA according to claim 2, wherein said DNA consists of CH4' (SEQ ID NO:1, 3–217).

7. An isolated DNA according to claim 2, wherein said DNA consists of CH5 (SEQ ID NO: 1, 359–440).

8. An isolated DNA according to claim 2, wherein said DNA consists of M2" (SEQ ID NO:4, 420–443).

\* \* \* \* \*